United States Patent [19]

Calleson et al.

[11] 4,171,635
[45] Oct. 23, 1979

[54] APPARATUS FOR MEASURING SMOKE DILUTION IN A VENTED-FILTER CIGARETTE

[75] Inventors: Donald A. Calleson; Ned A. Sigmon, both of Durham, N.C.

[73] Assignee: Liggett Group Inc., Durham, N.C.

[21] Appl. No.: 956,019

[22] Filed: Oct. 30, 1978

[51] Int. Cl.² ............................................. G01N 15/08
[52] U.S. Cl. ............................................................ 73/38
[58] Field of Search ....................... 73/37, 38, 41, 49.8, 73/239

[56] References Cited

U.S. PATENT DOCUMENTS

| | | | |
|---|---|---|---|
| 3,386,281 | 6/1968 | Menge et al. | 73/38 X |
| 3,948,084 | 4/1976 | Heitmann et al. | 73/38 X |
| 3,991,605 | 11/1976 | Reuland | 73/38 |
| 4,052,892 | 10/1977 | Browne | 73/239 X |
| 4,127,025 | 11/1978 | Mills et al. | 73/38 |

Primary Examiner—Herbert Goldstein
Attorney, Agent, or Firm—J. Bowen Ross, Jr.; Michael L. Hendershot

[57] ABSTRACT

As a puff generator draws a volume of smoke and air through the vented-filter cigarette air is drawn from a ventilation cylinder to cause a piston to travel to a dead center position. The amount of movement of this piston is a measure of an amount of air drawn through the ventilation path of the filter by the puff generator. The amount of travel can be related to the total possible stroke of the piston so as to produce a digital read out of the degree of ventilation directly.

14 Claims, 3 Drawing Figures

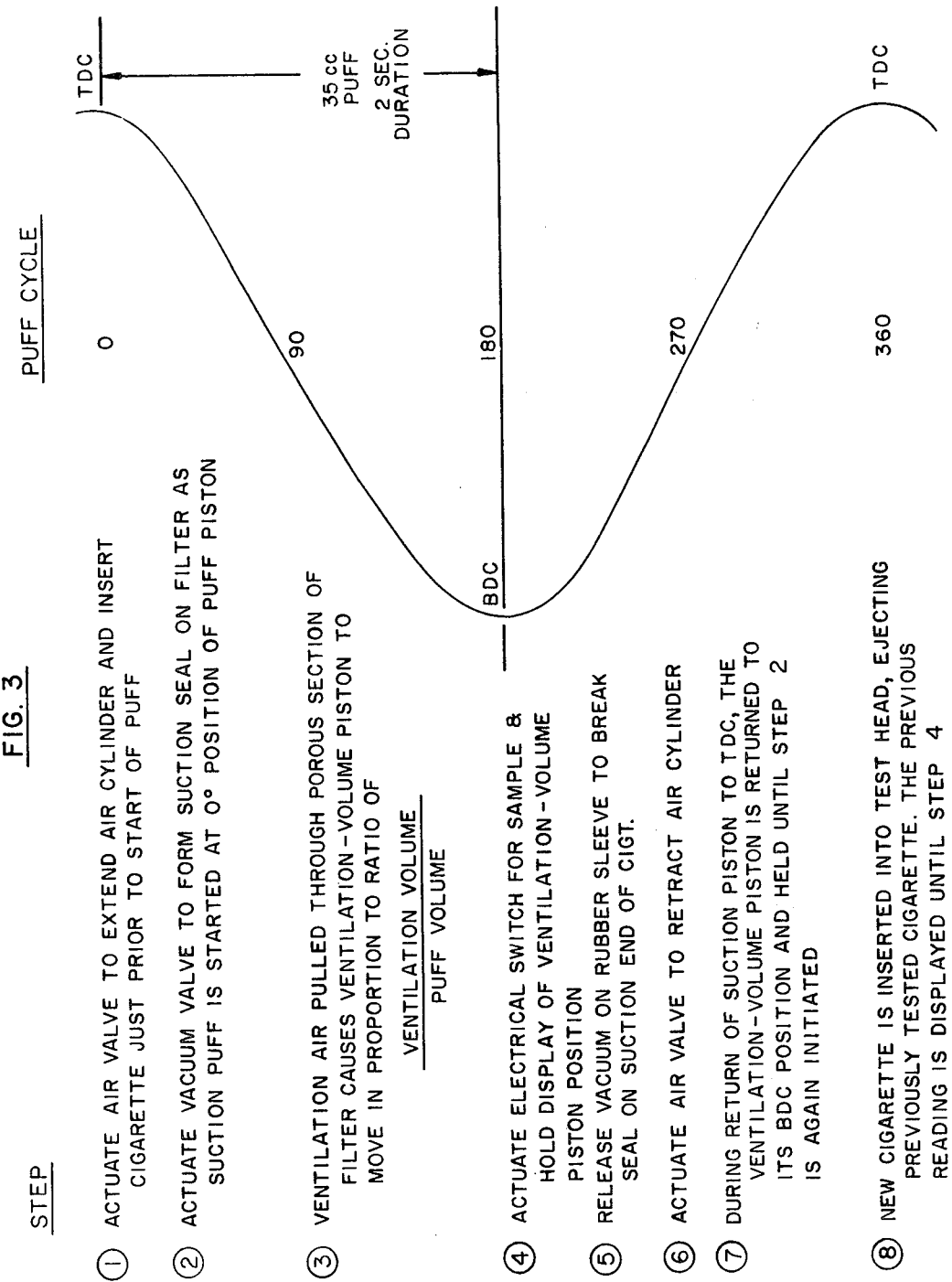

APPARATUS FOR MEASURING SMOKE DILUTION IN A VENTED-FILTER CIGARETTE

As is know, a significant number of cigarettes which are presently sold are made with vented-filters. During smoking, smoke is drawn from a tobacco column through a filter mass such as a cellulose acetate material within the filter and is mixed with air which is drawn in through vents in the filter. In some cases, the air and smoke are mixed within the filter while in other cases the air and smoke are drawn into a smoker's mouth separately.

The design and evaluation of such vented-filters require an accurate means of measuring the degree of smoke dilution caused by air ventilation. Generally, laboratory procedures require accuracy more than rapidity of measurement. However, the equipment which is usually available has not been ideally suited to production quality control needs which require a rapid reliable method of measurement.

Various methods for measuring ventilation are described in the known literature. These are generally of two types, i.e. a puff-method type and a steady-state type to measure the rate of airflow. However, in both cases, the measurement of the rate of air flow through the ventilation path is a main difficulty. For example, in some cases, measurement of the air flow rate is carried out with a ball-float flowmeter. However, this introduces errors due to the airflow resistance in the flowmeter itself. In other cases, use is made of an electrical type hotwire anemometer to measure the air rate flow. However, in this case, the method is expensive and is subject to calibration shifts. Further, both methods suffer from the fact that air flow rate is not the real parameter desired. Rather, the quantity of air flow through the ventilation path relative to the total air drawn through the mouth-end of the cigarette is the desired parameter.

As is known, instruments which use the puff-method generally utilize a soap-bubble technique, also referred to as a spirometer. While the accuracy of this method is usually good enough for quality control purposes, it has been cumbersome and slow to use. Further, this technique does not lend itself to automation.

As is known, the degree of air ventilation is dependant upon specified system component parameters, such as porosity of filter plugwrap paper, resistence to airflow of perforated tipping paper and resistence to airflow of both the cigarette filter and the cigarette tobacco column. The combined effect of these components, both due to initial variations and to variations in assembly techniques, produces a potentially large variability in the ventilation in the finished cigarettes. Accordingly, there is a need for an instrument which can be used to measure the degree of smoke dilution immediately after manufacture. Ideally, this instrument should be accurate, rapid and require no calculation or conversion to obtain the ventilation number.

Accordingly, it is an object of this invention to provide an apparatus for accurately determining the degree of smoke dilution caused by air ventilation in a rapid manner.

It is another object of the invention to provide a relatively simple apparatus for determining the degree of smoke dilution caused by air ventilation in a vented-filter cigarette.

It is another object of the invention to provide an automated apparatus for testing the ventilation characteristics of a series of vented-filter cigarettes.

It is another object of the invention to provide an apparatus which can be used to measure the degree of smoke dilution in a vented-filter cigarette immediately after manufacture.

Briefly, the invention provides an apparatus for measuring the degree of smoke dilution caused by air ventilation in a vented-filter cigarette which is comprised of relatively simple components.

The apparatus includes a sample holder having a chamber for receiving a vented-filter end of a vented-filter cigarette, a suitable means for sealing the chamber in which the filter end is mounted from the exterior, a puff generator for drawing a predetermined volume of smoke through the cigarette as well as air from the sealed chamber and through the filter of the cigarette, a ventilation cylinder connected to the chamber and a piston disposed in the cylinder. The piston is disposed in the cylinder to define a pre-determined volume in communication with the chamber and is moveable in a closing sense in response to the puff generator drawing a volume of air from the chamber to reduce the volume in the cylinder.

In addition, the apparatus includes a means of displaying a numerical value indicative of the ratio of the amount of reduced volume in the ventilation cylinder to the volume drawn by the puff generator.

In one embodiment, the sample holder is provided with a second chamber adjacent to the chamber in which the filter end of the cigarette is located and sealed. This second chamber communicates directly with a puff generator which is formed by a cylinder and piston arrangement. The chamber which surrounds the filter of a cigarette communicates directly with the ventilation cylinder and piston arrangement. The respective pistons are arranged so that at the beginning of a puff cycle, the piston of the puff generator is in a top dead center position. At the same time, the piston of the ventilation cylinder is in a bottom dead center position. The two cylinder and piston arrangements are calibrated with respect to each other so that the total stroke of the piston of the puff generator from a top dead center position to a bottom dead center position represents a known volume of suction. Generally, this volume is a conventional 35 cubic centimeter volume. The total stroke of the piston of the ventilation cylinder from the bottom dead center position to a top dead center position defines the same volume.

In this embodiment, after a cigarette has been mounted in the sample holder, the puff generator draws a volume of smoke and air into the cylinder upon retraction of the piston. At the same time, air is drawn through the ventilation path in the filter from the surrounding chamber. Since this chamber communicates directly with the ventilation cylinder, the piston in the ventilation chamber is caused to move from the bottom dead center position towards the top dead center position. By calibrating the actual amount of movement of the piston to the total possible stroke of the piston, a measure of the smoke dilution caused by the air ventilation can be obtained.

The means for displaying the numerical value indicative of the ratio of the amount of reduced volume in a ventilation cylinder to the pre-determined volume of the puff generator includes a linear electrical transducer and a read-out means. The transducer serves to measure the movement of the ventilation cylinder piston in response to the movement of the puff generator piston while the read-out means serves to display the numerical value of the ratio of the actual movement of the ventilation piston to the distance between the two dead center positions of the ventilation piston. With an output voltage set to be zero at the bottom dead center position and ten at full travel, i.e. the top dead center position, the read out means can be made to read directly in percent ventilation of the cigarette.

In another embodiment, the apparatus utilizes a reciprocally mounted hollow rod for pushing a vented-filter cigarette into the chamber of the sample holder. In this case, the hollow rod has a bore in communication with the filter end of the cigarette as well as in direct communication with a cylinder in which a piston is slidably mounted in the form of a puff generator. A separate means is also provided for reciprocating the hollow rod so as to feed each of a series of vented-filter cigarettes sequentially between the rod and the holder for inspection into the holder.

In this embodiment, the sealing means includes an expandable rubber sleeve which is mounted in the holder so as to engage about the end of the cigarette filter within the holder and the end of the hollow rod. In addition, a vacuum port is provided in the holder to communicate with the rubber sleeve in order to expand the sleeve in response to a vacuum being drawn in the port from a suitable vacuum source. In this way, when the sleeve is expanded, a cigarette can be easily inserted into the holder while elimination of the vacuum allows the sleeve to collapse into sealing engagement about the filter and hollow rod.

The means for reciprocating the hollow rod may be in the form of an air cylinder with a piston connected to the hollow rod. This air cylinder is connected to an air source.

In this embodiment also, the pistons of the puff generator and the ventilation cylinder may be provided with fingers which are disposed in axial alignment. In this case, a return movement of the piston of the puff generator from the bottom dead center position to the top dead center causes engagement of the fingers and pulling of the ventilation piston back to a bottom dead center position for a subsequent test sample.

These and other objects and advantages of the invention will become more apparent from the following detailed description taken in conjunction with the accompanying drawings wherein:

FIG. 3 illustrates a timing sequence of operations in accordance with the invention;

Figure 1:
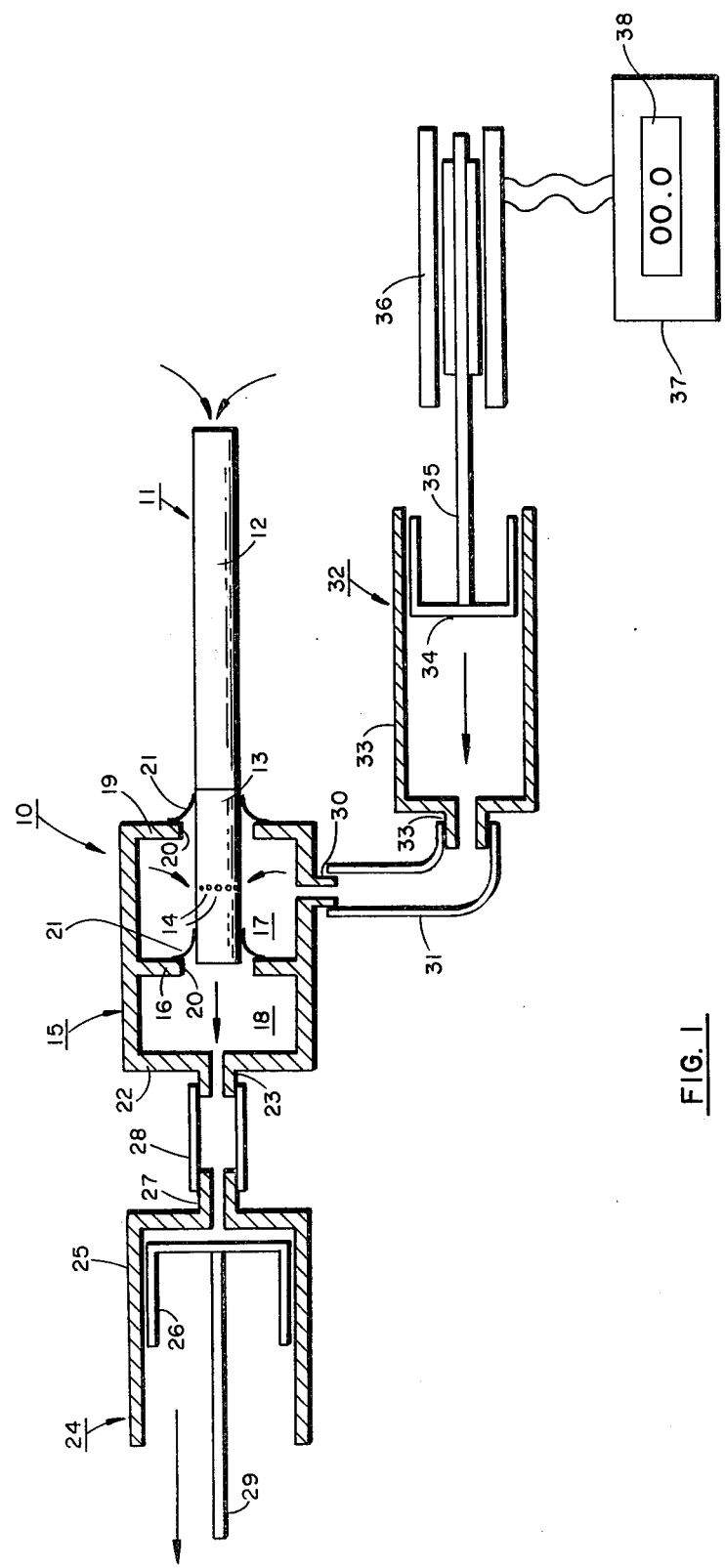
FIG. 1 illustrates a schematic view of an apparatus constructed in accordance with the invention.

Referring to FIG. 1, the apparatus 10 for measuring the degree of smoke dilution caused by air ventilation is adapted for use with a vented-filter cigarette 11 which is manufactured with a tobacco column 12 attached to a filter 13 of vented construction. As indicated, the filter end of the cigarette 11 is provided with a plurality of ventilation openings 14 for drawing air into and through the filter 13 during smoking of the cigarette 11. The cigarette 11 is of generally conventional structure and need not ne further described.

The apparatus includes a sample holder 15 of generally block shape or cylindrical construction sub-divided by a partition 16 into two chambers 17, 18. The partition 16 and a forward wall 19 of the holder 15 are provided with aligned apertures 20 to receive the filter end of the cigarette 11. In addition, suitable sealing means in the form of annular rubber rings or the like 21 are secured on the partition 16 and the forward wall 19 to seal the filter end of the cigarette 11 within the chamber 17. The rear wall 22 of the holder 15 is also provided with a small aperture 20 which communicates directly with the second chamber 18 and with a spigot 23.

The apparatus also includes a puff generator 24 which is constructed with a cylinder 25 and a piston 26. The cylinder 25 has a spigot 27 which is connected by a suitable sleeve 28 to the spigot 23 of the sample holder 15 while the piston 26 is reciprocally mounted within the cylinder 25 in any suitable fashion via a rod 29.

The puff generator 24 is of generally conventional structure and is used to displace a volume of 35 cubic centimeters since this most closely approximates actual smoking conditions. Generally, the cylinder 25 is made of ground glass while the piston 26 is made of graphite in order to reduce frictional resistance.

As shown, the sealed chamber 17 is connected via a spigot 30 and a suitable tube 31 to a ventilation cylinder and piston arrangement 32. This arrangement 32 can be constructed in identical fashion to the puff generator 24 and includes a cylinder 33 which is connected by a spigot 33' to the tube 31 and a piston 34 which is slidably mounted within the cylinder 33. In addition, the piston 34 is connected to a rod 35 which extends to a linear electrical transducer 36. This transducer 36 is constructed in a conventional manner to sense the movement of the rod 35 and to emit a signal representative of the amount of movement of the rod 35. The transducer 36 is connected to a read-out means 37 by suitable lines 38 in order to deliver a signal thereto indicative of the amount of movement of the piston 34 and rod 35. The read-out means 37 is calibrated in suitable fashion to display a numerical value on a display 38 indicative of the movement of the piston 34.

In operation, the piston 26 of the puff generator is positioned in a top dead center position (as shown in FIG. 1) while the piston 34 of the ventilation cylinder 33 is positioned in a bottom dead center position (as shown in FIG. 1). In this position, the piston 34 defines a pre-determined volume within the cylinder 33 which is in communication with the sealed chamber 17. The bottom dead center position of the ventilation cylinder 33 is calibrated with respect to the puff generator 24 so that the top dead center position of the piston 34 corresponds to the bottom dead center position of the piston 26 of the puff generator 24.

In order to measure the degree of smoke dilution caused by air ventilation, the filter end 13 of a cigarette 11 is inserted into the sealed chamber 17 of the holder 15. At this time, the seals 21 envelop the filter end 13 so that the ventilation openings 14 are in direct communication with the sealed chamber 17. The puff generator 24 is then actuated to draw the piston 26 from the top dead center position to a bottom dead center position. This movement occurs over a two-second time interval, at this time, a pre-determined volume, e.g. 35 cubic centimeters of smoke and air is drawn into the cylinder 25 from the chamber 18 of the sample holder 15. In this regard, the smoke is drawn through the tobacco column 12 and filter 13 directly into the chamber 18 while air is drawn from the sealed chamber 17 through the ventilation openings 14 in the filter 13 and through the filter 13 into the chamber 18. Because the air is drawn through the sealed chamber 17, the piston 34 in the ventilation cylinder 33 is drawn from the bottom dead center position towards the top dead center position. The amount of travel corresponds to the amount of air drawn out of the chamber 17 into the puff generator 24. During this time, the linear electrical transducer 36 measures the travel of the rod 35, and thus the piston 34, and produces an output voltage which is a measure of the travel of the piston 34. With an output voltage set to be zero at the bottom dead center position of the piston 34 and ten at full travel, i.e. should the piston 34 reach the top dead center position, the display 38 of the readout means 37 can be made to read directly in percent of ventilation of the cigarette. In essence, the readout means displays a numerical value indicative of the ratio of the amount of travel of the piston 34 (the amount of reduced volume in the cylinder 33) to the total possible travel of the piston 34 (the pre-determined volume displaced within the puff generated 24).

It is to be noted that frictional resistance of the ventilation piston 34 and the transducer 36 would cause a lesser displacement than the puff generator piston 26. However, because of the graphite and glass construction of the cylinder and piston arrangements 24, 32, this error is small. Also, static and dynamic friction are the same with the graphite-glass construction. Since the friction error can be measured, the error can be eliminated by adjustably mounting the ventilation cylinder 33 and piston 34 at a downwardly directed angle to a horizontal plane. In this manner, the force of gravity in the piston 34 can be adjusted to equal the frictional resistance so that displacement becomes a function only of the ventilation volume generated.

Figure 2:
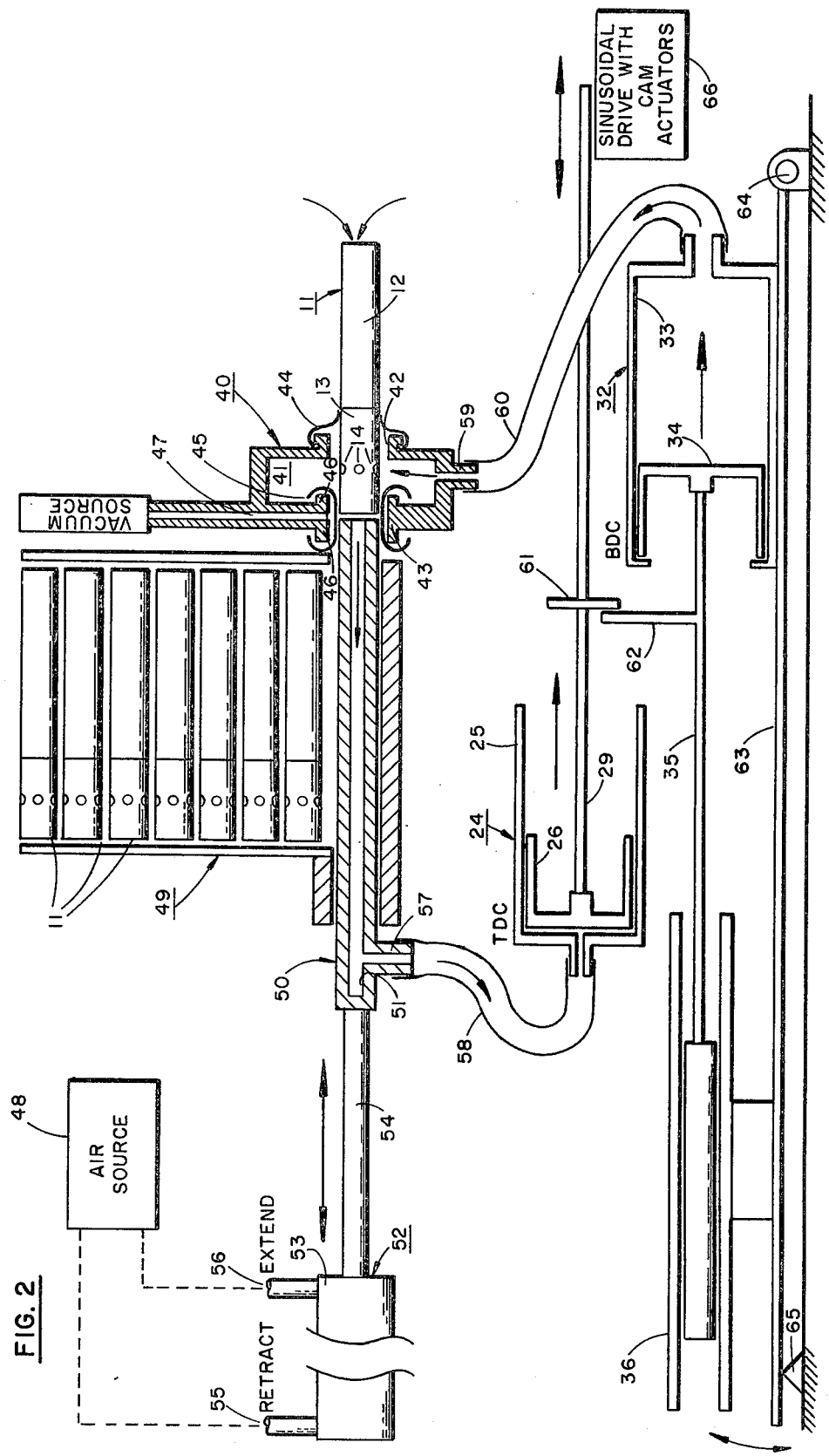
FIG. 2 illustrates a schematic view of an automated apparatus constructed in accordance with the invention.

Referring to FIG. 2, wherein like reference characters indicate like parts as above, the apparatus for measuring the degree of smoke dilution may be constructed for automated use. In this regard, the sample housing 40 has a single chamber 41 and a pair of openings 42, 43 which are aligned so as to receive a filter end 13 of a cigarette 11. In addition, a seal 44 such as a rubber dam seal is disposed over the forward opening 42 to seal against a received cigarette. Also, an expandable rubber sleeve 45 is positioned about the other opening 43 to seal against the end of the cigarette 11. As shown, this rubber sleeve 45 envelopes a pair of flanges 46 of the holder about the opening 43. In addition, the holder 40 has a vacuum port 47 which communicates with the outer periphery of the rubber sleeve 45 and a suitable vacuum source 48 such that upon application of the vacuum within the port 47, the sleeve expands radially to permit the passage of a cigarette 11 therethrough.

The apparatus also has a gravity feed hopper 49 for feeding each of a series of cigarettes into a position adjacent to the holder 40 and aligned with the openings 42, 43.

The apparatus also has a reciprocally mounted hollow rod 50 for pushing a cigarette 11 from the hopper 49 into the holder 40 with the filter 13 positioned within the chamber 41. As shown, the rod 50 has a bore 51 in communication with the filter end of the cigarette in the chamber 41. A suitable means 52 is also provided for reciprocating the hollow rod 50. This means 52 is in a form of an air cylinder 53 and a piston 54 which connects to the hollow rod 50. The air cylinder 53 has suitable connections 55, 56 at opposite ends which are connected, for example, to the air source 48 and serve to retract and extend the rod 54 in response to air being drawn on either side of a piston (not shown) located within the cylinder 53.

As shown, the hollow rod 50 also has a hollow stub 57 which is connected via a tube 58 to the cylinder 25 of the puff generator 24. In like manner, the chamber 41 of the holder 40 communicates via a spigot 59 and tube 60 with the cylinder 33 of the ventilation cylinder and piston arrangement 32.

As is also shown, the rods 29, 35 of the puff generator 24 and the ventilation cylinder and piston arrangement 32 are provided with fingers 61, 62 which are disposed in alignment for puposes as explained below.

Further, the ventilation cylinder 33 and transducer 36 are mounted on a platform 63 which is, in turn, pivotally mounted on a pivot 64 at one end. The opposite end of the platform 13 rests on a suitable support 54. The platform 63 can be pivoted relative to the horizontal and supported in that position by the support 65.

As shown, the apparatus also includes an electric motor assembly 66 which is provided with a sinusoidal drive with cam actuators (not shown).

In operation, a series of cigarettes 11 are placed into the gravity feed hopper 48. Next, with the motor assembly 66 switched on, the hollow rod 50 is programmed to retract from the position shown by a suitable cam operated air switch driven by the motor assembly 66. This permits a cigarette to drop into position in front of the push rod 50. Next, the air cylinder 52 is actuated to push the rod 50 forward to insert the cigarette 11 into the holder 40 through the rubber seals 44, 45. During this time, vacuum is drawn through the port 47 so that the rubber sleeve 45 is expanded to allow passage of the cigarette. As shown as the forward stroke of the rod 50 is completed, a cam operated switch (not shown) releases the vacuum seal 45 allowing the seal 45 to collapse around the end of the cigarette and the rod 50 forming a tight seal. At this point, the piston 26 of the puff generator is at the top dead center position and starts to pull a 35 cubic centimeter puff through the flexible tube 58 and hollow rod 50. The sealed chamber 41 in the holder 40 is partially evacuated by air being drawn in through the ventilated filter 13. This causes the ventilation piston 34 to translate from the bottom dead center position to displace a volume equivalent to the ventilation volume. At the end of the puffing stroke of the piston 26, a cam driven electrical switch (not shown) in the motor assembly 66 samples the signal from the transducer 36 and holds this signal in storage until the next cigarette is measured. The signal from the transducer 36 can be displayed, as above, on a digital display such as a panel meter as a percentage of full scale travel. As above, full scale travel of the ventilation piston 34 represents 100% ventilation.

As the piston 26 starts a return stroke, cam actuated air switches (not shown) in the motor assembly 66 sequentially apply vacuum to open the sleeve 45 and to retract the rod 54 and push rod 50. The return of the piston 26 at the top dead center position causes the finger 61 on the rod 29 to engage the finger 62 on the rod 35. This, in turn, causes the return of the ventilation piston 35 to the fully extended bottom dead center position. The piston 34 is held in this position by the finger 61 until the cycle is repeated by the start of another puff.

The timing sequence of the motor assembly 66 with respect to the sinusoidal motion of the puff generator system 26 is illustrated in FIG. 3.

The operation of this ventilation measuring apparatus is completely automated and requires only the loading of cigarettes into the hopper 48 and then the actuation of the motor assembly 66. A printer can also be provided to automatically record the meter display as each cigarette is tested.

What is claimed is:

1. An apparatus for measuring the degree of smoke dilution caused by air ventilation in a vented-filter cigarette, said apparatus comprising
 a sample holder having a chamber for receiving a vented-filter end of a vented-filter cigarette and means for sealing said chamber to the exterior thereof;
 a puff generator for drawing a predetermined volume of smoke through the cigarette in said sample holder and air from said chamber and through the filter of the cigarette in said sample holder;
 a ventilation cylinder connected to said chamber and a piston disposed in said cylinder to define a predetermined volume in communication with said chamber, said piston being movable within said cylinder to reduce said volume in response to said puff generator having a volume of air from said chamber; and
 means for displaying a numerical value indicative of the ratio of the amount of reduced volume in said cylinder to said predetermined volume.

2. An apparatus as set forth in claim 1 which furthur comprises means for positioning a series of cigarettes sequentially in said sample holder.

3. An apparatus for measuring the degree of smoke dilution caused by air ventilation in a vented-filter cigarette, said apparatus comprising:
 a sample holder having a first chamber for receiving a vented-filter end of a vented filter cigarette, a second chamber adjacent to and in communication with said first chamber, and sealing means for sealing said first chamber to the exterior thereof;
 a first cylinder in communication with said second chamber;
 a first piston slidably mounted in said cylinder for movement from a top dead center position to a bottom dead center position to draw a predetermined volume of smoke through the cigarette in said holder and air from said first chamber through the filter in said first chamber;
 a second cylinder in communication with said first chamber;
 a second piston slidably mounted in said second cylinder to define a predetermined volume within said second cylinder in communication with said first chamber, said second piston being mounted for movement from a bottom dead center position towards a top dead center position to reduce said predetermined volume in said second cylinder;
 a means for measuring the movement of said second piston in response to movement of said first piston; and
 a read-out means for displaying a numerical value indicative of the ratio of the actual movement of said second piston from said bottom dead center position to the distance between said positions of said second piston.

4. An apparatus as set forth in claim 2 wherein said read-out means includes a digital display.

5. An apparatus as set forth in claim 3 wherein said first cylinder is made of ground glass and said first piston is made of graphite.

6. An apparatus as set forth in claim 3 wherein said second cylinder and said second piston are disposed at a downwardly directed angle to a horizontal plane to compensate for friction between said second piston and said second cylinder.

7. An apparatus as set forth in claim 3 wherein said first chamber has a pair of axially aligned apertures for passage of a filter end of a cigarette and said sealing means includes a pair of annular seals, each seal being disposed about a respective aperture for sealing against the filter end.

8. An apparatus for measuring the degree of smoke dilution caused by air ventilation in vented-filter cigarettes, said apparatus comprising
 a sample holder having a chamber for receiving a vented-filter end of a vented-filter cigarette;
 a reciprocally mounted hollow rod for pushing a vented filter cigarette into said chamber, said rod having a bore in communication with the filter end of a vented-filter cigarette in said chamber;
 means for reciprocating said hollow rod;
 a first cylinder in communication with said bore;
 a first piston slidably mounted on said cylinder for movement from a top dead center position to a bottom dead center position to draw a predetermined volume of smoke through the cigarette in said holder and air from said chamber through the filter in said chamber;
 a second cylinder in communication with said chamber;
 a second piston slidably mounted on said second cylinder to define a predetermined volume within said second cylinder in communication with said chamber, said second piston being mounted for movement from a bottom dead center position towards a top dead center position to reduce said predetermined volume in said cylinder;
 a linear electrical transducer for measuring the movement of said second piston in response to movement of said first piston; and
 a read-out means for displaying a numerical value indicative of the ratio of the actual movement of said second piston from said bottom dead center position to the distance between said positions of said second piston.

9. An apparatus as set forth in claim 8 wherein said first piston carries a first finger and said second piston carries a second finger, said fingers being disposed in axial alignment whereby movement of said first position from said bottom dead center position to said top dead center position causes said fingers to engage and pull said second piston to said bottom dead center position thereof.

10. An apparatus as set forth in claim 8 wherein said means for reciprocating said hollow rod comprises an air cylinder connected to a vacuum source and a third piston reciprocally mounted in said air cylinder and connected to said hollow rod.

11. An apparatus as set forth in claim 8 which further comprises an expandable rubber sleeve mounted in said holder about a filter end of a cigarette in said chamber and a vacuum port in said holder communicating with said rubber sleeve to expand said sleeve in response to a vacuum in said port.

12. An apparatus as set forth in claim 11 which further comprises a vacuum source connected to said port, wherein said means for reciprocating said hollow rod includes an air cylinder connected to said vacuum soure and a third piston reciprocally mounted in said air cylinder and connected to said hollow rod.

13. An apparatus as set forth in claim 8 which further comprises a pivotally mounted platform having said second cylinder said transducer mounted thereon for movement in a plane inclined to a horizontal plane.

14. An apparatus as set forth in claim 8 which further comprises a gravity feed hopper for feeding a series of vented-filter cigarettes sequentially between said hollow rod and said holder for insertion into said holder.

* * * * *

UNITED STATES PATENT AND TRADEMARK OFFICE
CERTIFICATE OF CORRECTION

PATENT NO. : 4171635
DATED : October 23, 1979
INVENTOR(S) : Donald A. Calleson & Ned A. Sigmon It is certified that error appears in the above-identified patent and that said Letters Patent are hereby corrected as shown below:

Column 6, line 16, change "support 54" to --support 65--

In the Claims

Claim 4, column 7, line 64, change "claim 2" to --claim 3--
Claim 9, column 8, line 49, change "position" to --piston--
Claim 12, column 8, line 68, change "soure" to --source--
Claim 13, column 10, line 1, after "cylinder" insert --and--

Signed and Sealed this

Nineteenth Day of February 1980

[SEAL]

Attest:

SIDNEY A. DIAMOND

Attesting Officer

Commissioner of Patents and Trademarks